United States Patent [19]
de Castiglione et al.

[11] Patent Number: 5,100,873
[45] Date of Patent: Mar. 31, 1992

[54] IRREVERSIBLE PEPTIDE LIGANDS FOR BOMBESIN RECEPTORS, THEIR USE, AND PROCESS FOR MAKING THE SAME

[75] Inventors: Roberto de Castiglione; Mauro Galantino; Fabio Corradi; Luigia Gozzini, all of Milan; Marina Ciomei, Pavia; Isabella Molinari, Milan, all of Italy

[73] Assignee: Farmitalia Carlo Erba, Milan, Italy

[21] Appl. No.: 380,539

[22] Filed: Jul. 17, 1989

[30] Foreign Application Priority Data

Jul. 21, 1988 [GB] United Kingdom ................ 8817379
Mar. 28, 1989 [GB] United Kingdom ................ 8906900

[51] Int. Cl.$^5$ .......................... C07K 7/00; C07K 7/06; C07K 7/08; A61K 37/02
[52] U.S. Cl. ........................................ 514/15; 514/14; 514/16; 514/17; 530/327; 530/328; 530/329; 530/330
[58] Field of Search ....................... 514/14, 15, 16, 17, 514/18; 530/330, 331, 328, 329, 327

[56] References Cited

U.S. PATENT DOCUMENTS

4,314,999 2/1982 De Barbieri ........................ 424/177
4,428,875 1/1984 De Barbieri ................. 260/112.5 R
4,540,683 9/1985 De Barbieri et al. ................ 514/18

OTHER PUBLICATIONS

Coy et al., Journal of Biological Chemistry, vol. 263 No. 11 (1988), pp. 5056–5060.
Marki et al., Peptides. vol. 2, Suppl. 2 pp. 169–177, (1981).
Heinz-Erian et al., Am. J. Physiol. 252 (Gastrointest. Liver Physiol. 15): G439–G442, (1987).

Primary Examiner—Lester L. Lee
Assistant Examiner—A. M. Davenport
Attorney, Agent, or Firm—Oblon, Spivak, McClelland, Maier & Neustadt

[57] ABSTRACT

A peptide of formula (I):

A-B-C-D-Gln-Trp-Ala-Val-X-Y-T-W       (I)

wherein either:
(i) A represents a hydrogen atom, a Boc group or an acetyl group, one of B and C represents a pMel or mMel residue, and the other of B and C represents a sigma bond or a Gly, Leu-Gly, E-Leu-Gly or Gln-E-Leu-Gly, E, or E-Gly residue with E=Arg(A), arg(A), Lys(A), lys(A), Orn(A) and orn(A); or
(ii) A represents a hydrogen atom;
B represents a Glp-Arg-Leu-Gly residue;
C represents a pMel or mMel residue;
D represents a sigma bond or an Asn or Thr residue;
X represents a Gly or ala residue;
Y represents a sigma bond or a His($R_1$);
his($R_1$), Phe, phe, Ser, ser, Ala or ala residue,
T represents a sigma bond or a Leu, leu, Phe or phe residue;
W represents an OH, amino, pentylamino or phenethylamino group or a Met-$R_2$, Leu-$R_2$, Ile-$R_2$ or Nle-$R_2$ residue;
$R_1$ represents a hydrogen atom or a Tos, Dnp or Bzl group; and
$R_2$ represents an amino, hydroxy, methoxy or hydrazino group;
and its pharmaceutically acceptable salts are disclosed.

7 Claims, No Drawings

IRREVERSIBLE PEPTIDE LIGANDS FOR BOMBESIN RECEPTORS, THEIR USE, AND PROCESS FOR MAKING THE SAME

BACKGROUND OF THE INVENTION

1. Field of the Invention

The present invention relates to biologically active peptides, their pharmaceutically acceptable salts, and the processes for their preparation and application as therapeutic agents.

2. Discussion of the Background

In the present specification symbols and abbreviations are those commonly used in peptide chemistry (see Eur. J. Biochem. (1984) 138, 9–37). Consequently, the three-letter amino acid symbols denote the L configuration of chiral amino acids. D-amino acids are represented by small letters: e.g., ala=D-Ala. Other symbols and abbreviations used are: AA=amino acid; AcOEt=ethylacetate; AcOH=acetic acid; Bzl=benzyl; BBS=bombesin; Boc=t-butyloxycarbonyl; BuOH=-butyl alcohol; CCD=counter-current distribution; DCC=N,N'-dicyclohexylcarbodiimide; dec.=decomposition; DMAP=4-dimethylaminopyridine; DMF=Dimethylformamide; Dnp=2,4-dinitrophenyl; ECC= ethylchlorocarbonate; $Et_2O$=diethylether; Glp=L-pyroglutamic acid; h-GRP (or p-GRP)=human (or porcine) gastrin releasing peptide; HCl/AcOH=dry HCl in anhydrous acetic acid; HOBt=1-hydroxybenzotriazole; HPLC=hight performance liquid chromatography; i.c.v.=intracerebroventricular; MeOH=methyl alcohol; m.p.=melting point; mMel=m-bis(2-chloroethyl)amino-L-phenylalanine; n.d.=not determined; NMM=N-methylmorpholine; pMel=p-bis (2-chloroethyl) amino-L-phenylalanine; OSu=N-hydroxysuccinimidyl; TFA=trifluoroacetic acid; THF=tetrahydrofuran; TLC=thin layer chromatography; Tos=p-toluenesulphonyl; TsOH=p-toluenesulphonic acid; Z=benzyloxycarbonyl.

SUMMARY OF THE INVENTION

The invention provides peptides of formula (I)

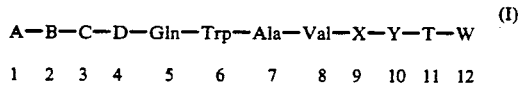

(I)

wherein:
A=H, Boc, Ac;

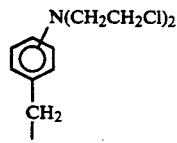

B = pMel, mMel (-Mel- = —HN—CH—CO—);

C=—(i.e., a sigma ($\sigma$) bond), Gly, Leu-Gly, E-Leu-Gly, Gln-E-Leu-Gly, E, E-Gly;
D=—(i.e., a $\sigma$ bond), Asn, Thr;
E=Arg(A), arg(A), Lys(A), lys(A), Orn(A), orn(A);
X=Gly, ala;
Y=—(i.e., a $\sigma$ bond), His($R_1$), his($R_1$), Phe, phe, Ser, ser, Ala, ala;
T=—(i.e., a $\sigma$ bond), Leu, leu, Phe, phe;
W=OH, $NH_2$, $NH(CH_2)_4CH_3$, $NH(CH_2)_2C_6H_5$, Met-$R_2$, Leu-$R_2$, Ile-$R_2$, Nle-$R_2$;
$R_1$=H, Tos, Dnp, Bzl;
$R_2$=$NH_2$, OH, OMe, NH-$NH_2$; and
wherein B and C can be inverted (i.e., B is in position 3 and C is in position 2); in this case, when A=H, the sequence Gln-Arg-Leu-Gly in the peptide may be changed to Glp-Arg-Leu-Gly.

DETAILED DESCRIPTION OF THE PREFERRED EMBODIMENTS

Salts of these peptides of formula (I) with pharmaceutically acceptable acids are also within the scope of the invention. Such acid addition salts can be derived from a variety of inorganic and organic acids such as sulfuric, phosphoric, hydrochloric, hydrobromic, hydroiodic, nitric, sulfamic, citric, lactic, pyruvic, oxalic, maleic, succinic, tartaric, cinnamic, acetic, trifluoracetic, benzoic, salicylic, gluconic, ascorbic and related acids.

Bombesin (BBS) is a tetradecapeptide of formula Glp-Gln-Arg-Leu-Gly-Asn-Gln-Trp-Ala-Val-Gly-His-Leu-Met-$NH_2$. It was originally isolated from the skin of a frog. The biological activity of this peptide resides in the C-terminal part of the molecule. BBS(6-14) nonapeptide is as active as the parent compound. The human counterpart of bombesin is a 27 amino acid peptide known as gastrin-releasing peptide (h-GRP).

Bombesin and bombesin-like peptides display a number of biological activities (J. H. Walsh (1983) in "Brain Peptides," D. T. Krieger, M. J. Brownstein and J. B. Martin (eds), Wiley Interscience Publ., pp. 941–960 ), including autocrine growth-promoting effects on human small cell lung carcinoma (SCLC) (F. Cuttitta et al. (1985) Cancer Survey, 4, 707–727), autocrine and/or paracrine stimulation of human prostatic cancer cell proliferation (M. Bologna et al., Cancer, in press) and modulation of the EGF receptor (I. Zachary and E. Rozengurt (1985) Cancer Surveys, 4 729–765).

In this case, a bombesin antagonist, by competing with the natural ligand for the receptor(s), would inhibit or modify the triggering of the cascade of events leading to abnormal cell proliferation. Different approaches in this direction have been followed by different research groups.

A series of C-terminal bombesin nona- and decapeptides, characterized by amino acid deletion, inversion or substitution, has been the object of a previous patent application by us (EP Patent Application No. 89102283.2). These peptides, however, like other BBS antagonists (A. Cowan (1988) TIPS, 9, 1–3) usually show only moderate affinity for the BBS receptor.

In the classical ligand-receptor model, an equilibrium exists between the dissociated and undissociated forms. In order to shift the equilibrium towards the formation of the ligand-receptor complex, in the present invention an alkylating moiety was introduced at the N-terminal sequence of bombesin analogues. Receptor affinity and selectivity, being bound to the C-terminal part of the sequence, are preserved, and a bond can be established between the BBS analogue and its receptor.

According to a general hypothesis, the irreversible ligand-receptor complex so formed would cluster with other receptors in clathrin-coated pits. The new complex is then internalized in coated vesicles which rapidly shed their clathrin coats and fuse with other vesicles to form endosomes.

In the normal situation, ligand-receptor dissociation takes place probably as a consequence of the low pH inside the endosomes. The receptors so released are then recycled wholly or in part to the cell membrane.

When bound to the receptor, the ligands of the present invention make this receptor's roundtrip impossible. Consequently, the present alkylating bombesin analogues behave always as bombesin receptor antagonists, regardless of their intrinsic agonistic or antagonistic properties.

Both types of alkylating analogue peptide of the invention can therefore find application in the therapy of human neoplasms which are modulated in their growth and progression by peptides of the GRP family, either directly or in concert with other growth factors. In addition, these alkylating analogues can be used in the management of the clinical symptoms associated with these diseases and due to hypersecretion of GRP-like peptides.

The compounds of the invention can be administered by the usual routes, for example, parenterally, e.g. by intravenous injection or infusion, or by intramuscular, subcutaneous, intracavity and intranasal administration.

The dosage depends on the age, weight and condition of the patient and on the administration route. On the basis of in vitro and in vivo data in mice, the therapeutic doses in humans for these materials is in the range 10 ng kg$^{-1}$ to 10 mg kg$^{-1}$, once to 6 times daily.

The invention also provides pharmaceutical compositions containing at least one compound of formula (I) as the active substance, in association with one or more pharmaceutically acceptable excipients. In the compositions, the present peptide of formula (I) may be present in an amount of from 1 wt. % to 99 wt. %.

The pharmaceutical compositions of the invention are usually prepared following conventional methods and are administered in a pharmaceutically suitable form.

For instance, solutions for intravenous injection or infusion may contain as carrier, for example, sterile water or, preferably, they may be in the form of sterile aqueous isotonic saline solutions.

Suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Furthermore, according to the invention there is provided a method of treating neuroendocrine neoplasms, such as small cell lung carcinoma and prostatic carcinoma or the clinical symptoms associated with these diseases in a patient in need of it, comprising administering to the said patient a composition of the invention.

The synthesis of the peptides of the invention may be accomplished by classical solution methods. The synthesis consists essentially of appropriate successive condensations of protected amino acids or peptides. The condensations are carried out so that the resulting peptides have the desired sequence of amino acid residues.

The amino acids and peptides, which can be condensed according to methods known in peptide chemistry, have the amino and carboxyl groups, not involved in peptide bond formation, blocked by suitable protecting groups capable of being removed by acid or alkali treatment or by hydrogenolysis.

For the protection of the amino group the following protective groups may, for example, be employed: benzyloxycarbonyl, t-butoxycarbonyl, trityl, formyl, trifluoracetyl, o-nitrophenylsulphenyl, 4-methyloxybenzyloxycarbonyl, 9-fluorenylmethoxycarbonyl, 3,5-dimethoxy-α-α'-dimethylbenzyloxycarbonyl or methylsulphonylethoxycarbonyl.

For the protection of the carboxyl group the following protective groups may, for example, be employed: methyl, ethyl, t-butyl, benzyl, p-nitrobenzyl or fluorenylmethyl, amide, hydrazide, t-butoxycarbonyl hydrazide or benzyloxycarbonyl hydrazide.

The hydroxy functions of hydroxy amino acids and the imino function of histidine may be protected by suitable protecting groups (throughout all the synthesis or only during a few steps) or may be unprotected. For the protection of the hydroxy function the following protective groups may, for example, be employed; t-butyl, benzyl, acetyl. For the protection of the imidazole imino function the following groups may, for example, be used: 2,4-dinitrophenyl, tosyl, benzyl. Deprotecting reactions are carried out according to methods known per se in peptide chemistry.

The condensation between an amino group of one molecule and a carboxyl group of another molecule to form the peptidic linkage may be carried out through an activated acyl-derivative such as a mixed anhydride, an azide or an activated ester, or by direct condensation between a free amino group and a free carboxyl group, in the presence of a condensing agent such as dicyclohexylcarbodiimide, alone or together with a racemization preventing agent, such as N-hydroxysuccinimide or 1-hydroxybenzotriazole, or together with an activating agent such as 4-dimethylamino-pyridine. The condensation may be carried out in a solvent such as dimethylformamide, dimethylacetamide, pyridine, acetonitrile, tetrahydrofuran or N-methyl-2-pyrrolidone.

The reaction temperature may be from −30° C. to room temperature. The reaction time is generally from 1 to 120 hours.

The scheme of synthesis, the protecting groups and condensing agents are selected so as to avoid the risk of racemization.

Other features of this invention will become apparent in the course of the following descriptions of exemplary embodiments which are given for illustration of the invention and are not intended to be limiting thereof.

$R_f$ values were determined on pre-coated plates of silica gel 60 $F_{254}$ (Merck), layer thickness 0.25 mm, length 20 cm, using the following development systems:
System A: ethyl acetate/benzene/acetic acid/water=500/500/100/50 by volume (upper phase)
System B: ethyl acetate/benzene/acetic acid/water=500/500/200/75 by volume (upper phase)
System C: n-butanol/acetic acid/water=600/150/150 by volume
System D: chloroform/methanol/NH$_4$OH 30%=488/338 150 by volume
System E: chloroform/methanol=90/10 by volume
System F: toluene/ethylacetate/acetic acid/water=100/100/20/10 by volume TLC analyses were carried out at a temperature ranging from 18° C. to 25° C.: the $R_f$ values can therefore change±5%.

High performance liquid chromatography (HPLC) was carried out using a Hewlett-Packard 1084B apparatus equipped with a UV detector operating at 210 nm. The peptides were separated on a 4×250 mm Lichrosorb RP 18 5μ column. The following solvents were used:

A) 0.02M KH$_2$PO$_4$ adjusted to pH 3.5 with 3% H$_3$PO$_4$CH$_3$CN=9/1 by volume B) 0.02M KH$_2$PO$_4$ adjusted to pH 3.5 with 3% H$_3$PO$_4$/CH$_3$CN=3/7 by volume.

The elution was programmed with a linear gradient from 60% to 90% B over a period of 20 min (System A) or from 30 to 70% B over a period of 15 min (System B), and then isocratically for 15 min, with a flow rate of 1 ml/min.

The peptides were characterized by their retention time (RT). Amino acid analysis was carried out on acid hydrolysates (either at 110° C. for 22 h in 6N HCl+0.1% phenol or at 100° C. for 16 h in 3N mercaptoethansulfonic acid, both under N$_2$). Only natural amino acid residues were determined. Due to partial decomposition in normal hydrolysis conditions, Trp was determined only in hydrolysates with the sulfonic acid.

The binding affinity of the compounds of the present invention for bombesin receptors was determined on mouse Swiss 3T3 fibroblasts (I. Zachary and E. Rozengurt (1985) *Proc. Natl. Acad. Sci.* USA, 82, 7616-7620) (Table 1).

The effect on mitogenesis was determined in quiescent and confluent Swiss 3T3 cells maintained in serum free medium (A. N. Corps et al (1985) *Biochem J.* 231, 781-785). In a first set of experiments, analogues were given alone or in combination with bombesin. In a second set of experiments, cells were pre-treated with the alkylating peptides, washed, left at 37° C. for 24 hours and then challenged with bombesin. In both cases, DNA synthesis was evaluated as [H$^3$]thymidine incorporation (Table 2).

Mitogenic effect of bombesin and its analogues were also evaluated as activation of the proteintyrosin kinase that phosphorylates a 115 KD protein (p115) associated with the bombesin receptor complex (D. Cirillo et al. (1986) *Mol. Cell. Biol.* 6, 4641-4649) (Table 3).

In addition, exposure to these peptides in the 0.1-50 μM range was associated with significant reduction in the growth of SCLC cell lines (such as NCI-H345, NCI-N592, NCI-H128), as well as of prostatic carcinoma cell lines (such as DU145 and PC3).

Parenteral administration of these peptides at doses ranging between 10 ng kg$^{-1}$ to 10 mg kg$^{-1}$ to nude mice was associated with significant growth reduction of the above mentioned transplanted human SCLC and prostatic carcinoma cell lines.

Peripheral and central effects have been evaluated in the rat, respectively in vitro, as urinary bladder contraction (M. Broccardo et al. (1975) *Br. J. Pharmac.*, 55, 221-227) and in vivo by i.c.v. administration, as grooming behaviour (A. Cowan et al. (1985) *Life Sciences*, 37, 135-145), both in the absence and in the presence of bombesin.

EXAMPLE 1

Boc-pMel-Gln-Trp-Ala-Val-Gly-OH (III)

Step 1: Boc-pMel-OH (I)

0.684 g (1.85 mmol) of H-pMel-OEt.HCl (F. Bergel and J. A. Stock (1954) *J. Chem. Soc.* 2409-2417) and 0.485 g (2.2 mmol) of (Boc)$_2$O were dissolved in 40 ml of water and 8 ml of t-BuOH. The solution was adjusted to pH 10 with 1N NaOH, stirred for 15 min, then 40 ml of water and 110 ml of MeOH were added, and the pH brought to 13.5 with 1 NaOH.

The reaction mixture was stirred for 1 hr a room temperature, then brought to pH 8.5 with 1N HCl and concentrated in vacuo. The aqueous solution was washed with n-hexane (4×30 ml), then cooled to −5° C., acidified to pH 2 with 1N HCl under stirring, and extracted with cooled AcOEt (4×30 ml). The organic layers were combined, washed to neutrality with saturated solution of NaCl, dried over anhydrous Na$_2$SO$_4$, filtered and evaporated in vacuo.

The residue was dissolved in a mixture of CH$_2$Cl$_2$/AcOH 99/1 and purified by flash chromatography on silica gel eluting with the same solvent mixture. 0.7 g (77.8% yield) of product I were obtained as an oil: R$_{fA}$ 0.70.

Step 2: Boc-pMel-Gln-Trp-Ala-Val-Gly-OBzl (II)

0.6 g of Boc-pMel-OH (I) (1.48 mmol) were dissolved in 10 ml of anydrous THF. The solution was cooled to −20° C., and 0.16 ml (1.48 mmol) of NMM and 0.15 ml (1.48 mmol) of ECC were successively added. After stirring at this temperature for 2 min, a cold solution of 1.02 g (1.48 mmol) of H-Gln-Trp-Ala-Val-Gly-OBzl.HCl (UK patent application no. 8808768.9), and 0.16 ml (1.48 mmol) of NMM in 10 ml of anhydrous DMF, was added. The reaction mixture was stirred for 2 h at −10° to −15° C., then filtered and evaporated in vacuo.

The residue was dissolved in 20 ml of DMF and poured dropwise into 40 ml of a 10% solution of citric acid at 5° C. The mixture was stirred for 1 h at a temperature below 10° C., then filtered and washed with water to neutrality. 1.4 g (91.5% yield) of product II were obtained: R$_{fB}$ 0.48

Step 3: Boc-pMel-Gln-Trp-Ala-Val-Gly-OH (III)

0.44 g of 10% Pd/C and 24 ml of a pre-warmed solution made from 1.2 ml of HCOOH, 3.3 ml of NMM and 100 ml of MeOH, were added to a solution of 1.2 g (1.16 mmol) of Boc-pMel-Gln-Trp-Ala-Val-Gly-OBzl (II) in 24 ml of anhydrous DMF. The reaction mixture was stirred for 15 min at 40° C., then cooled to room temperature, filtered and evaporated in vacuo. The residue was dissolved in DMF and precipitated with AcOEt, giving 1.1 g of crude product. This was purified by counter current distribution in the solvent system: water/DMF/n-BuOH/AcOEt=40/3/20/80. Fractions containing the pure product were pooled and evaporated in vacuo. The residue was ground in DMF, MeOH and AcOEt, giving 0.680 g (63% yield) of product III: R$_{fD}$ 0.54; RT$_A$ 8.4; AA ratios; Glu 0.93 (1), Gly 0.99 (1), Ala 0.99 (1), Val 1 (Trp and pMel n.d.).

EXAMPLE 2

Boc-pMel-Gln-Trp-Ala-Gly-His(Dnp)-Leu-Met-NH$_2$ (IV)

To a solution of 0.330 g (0.35 mmol) of Boc-pMel-Gln-Trp-Ala-ValGly-OH (III) in 3 ml of anhydrous DMF, 0.053 g (0.39 mmol) of anhydrous HOBt, 0.081 g (0.39 mmol) of DCC, 0.235 g (0.39 mmol) of H-His(Dnp)-Leu-Met-NH$_2$.HCl (F. Angelucci and R. de Castiglione (1975) *Experientia*, 507-508) and 0.043 ml (0.39 mmol) of NMM were successively added. The reaction mixture was stirred at 0° C. for 1 h and at room temperature for 30 h, then it was filtered and evaporated in vacuo.

The residue was dissolved in 3 ml of anhydrous DMF, poured dropwise into 30 ml of an aqueous solution of 6 g NaCl and 3 g citric acid at a temperature below 10° C. After stirring for 1 h at a temperature <10° C., the suspension was filtered and the product was washed to neutrality. The crude material was evaporated twice from 10 ml of anhydrous DMF, then dissolved in 3 ml of anhydrous DMF and poured dropwise into 30 ml of an aqueous solution of 1.5 g NaHCO$_3$ and 6 g NaCl at a temperature below 10° C. The mixture was stirred for 1 h, then filtered and washed with water to neutrality, giving 0.5 g (95.6% yield) of product IV: R$_{fD}$=0.84; RT$_A$ 21.2; AA ratios: Trp 0.97 (1), Glu 1.00 (1), Gly 1, Ala 1.00 (1), Val 1.00 (1), Met 1.10 (1), Leu 1.04 (1) (pMel and His(Dnp) n.d.).

EXAMPLE 3

H-pMel-Gln-Trp-Ala-Val-Gly-His(Dnp)-Leu-Met-NH$_2$.HCl (V)

0.100 g (0.067 mmol) of Boc-pMel-Gln-Trp-Ala-Val-Gly-His(Dnp)-Leu-Met-NH$_2$ (IV) were made to react with 1 ml of 1.33N HCl/AcOH containing, 0.2 ml of 2-mercaptoethanol and 0.1 ml of anisole. The reaction mixture was stirred for 30 min at room temperature, then evaporated in vacuo. The residue was ground with Et$_2$O, giving 0.080 g (83.5% yield) of product V: R$_{fc}$=0.57; RT$_A$ 9.3; AA ratios: Glu 0.99 (1), Gly 0.98 (1), Ala 1.04 (1), Val 1.10 (1), Met 0.82 (1), Leu 0.81 (1) (Trp, pMel and His(Dnp) n.d.).

EXAMPLE 4

Boc-pMel-Gln-Trp-Ala-Val-Gly-His-Leu-Met-NH$_2$ (VI)

0.4 g (0.27 mmol) of Boc-pMel-Gln-Trp-Ala-Val-Gly-His(Dnp)-Leu-Met-NH$_2$ (IV) were dissolved in 400 ml of anhydrous DMF, then 5.36 ml of 0.1M KH$_2$PO$_4$ (brought to pH 8.1 with 1N KOH) and 20 ml of 2-mercaptoethanol were added. The reaction mixture was stirred for 2 h at room temperature, then concentrated in vacuo. The residue was purified by counter-current distribution in the solvent system: water/n-BuOH/AcOH=40/35/1. Fractions containing the pure product were pooled and evaporated in vacuo, giving 0.35 g (theorical yield) of product VI: R$_{fc}$ 0.63; Rf$_D$ 0.82; RT$_A$ 14.2; AA ratios: Glu 1, Gly 1.00 (1); Ala 1.04 (1), Val 1.04 (1); Met 0.94 (1), Leu 1.02 (1), His 0.95 (1), Trp 0.88 (1) (pMel n.d.).

EXAMPLE 5

H-pMel-Gln-Trp-Ala-Val-Gly-His-Leu-Met-NH$_2$.2 HCl (VIII)

0.1 g (0.075 mmol) of Boc-pMel-Gln-Trp-Ala-Val-Gly-His-Leu-Met-NH$_2$ (VI) were deblocked as described in example 3, obtaining 0.089 g (91% yield) of product VII: R$_{fc}$ 0.45; RT$_B$ 11.3; AA ratios: Glu 1.06 (1), Gly 1.00 (1), Ala 0.99 (1), Val 1, Met 0.94 (1), Leu 0.96 (1), His 0.94 (1) (Trp and pMel n.d.).

EXAMPLE 6

Boc-pMel-Gln-Trp-Ala-Val-Gly-phe-Leu-Met-NH$_2$ (VIII)

0.15 g (0.16 mmol) of Boc-pMel-Gln-Trp-Ala-Val-Gly-OH (III) were dissolved in 12 ml of anhydrous DMF, and 0.023 g (0.169 mmol) of anydrous HOBt were added. To the solution, cooled at 0° C., 0.041 g (0.177 mmol) of DCC, 0.085 g (0.192 mmol) of H-phe-Leu-Met-NH$_2$.HCl (UK Patent Appl. no. 8808768.9, example 1-step 14) and 0.022 ml of NMM (0.192 mmol) were added successively.

After stirring for 15 min at 0° C., 0.002 g (0.016 mmol) of DMAP were added. The reaction mixture was stirred for 1 h at 0° C. and overnight at room temperature, then filtered and evaporated in vacuo. The residue was dissolved in 3 ml of DMF and poured dropwise into 30 ml of an aqueous solution of 3 g citric acid and 6 g NaCl, at a temperature below 10° C. After stirring for 1 h, the solid was filtered and washed with water to neutrality. The product was then dissolved in 10 ml of anhydrous DMF and evaporated in vacuo. The residue was ground with Et$_2$O, giving 0.190 g (88.8% yield) of crude compound VIII. A sample was purified by reverse phase semi-preparative HPLC using a linear gradient system of 0.05% TFA (A) and 0.05% TFA/CH$_3$CN=3/7 (B), from 70% to 90% B: R$_{fc}$ 0.85; RT$_A$ 18.4; AA ratios: Glu 0.90 (1); Gly 1.14 (1), Ala 1.02 (1), Val 0.99 (1); Met 0.94 (1), Leu 1.08 (1), phe 0.96 (1), Trp 0.96 (1) (pMel n.d.).

EXAMPLE 7

Boc-mMel-Gln-Trp-Ala-Val-Gly-OH (IX)

The title compound was obtained as described in Example 1, starting from Boc-mMel-OH, obtained in turn from H-mMel-OH (H.F. Gram et al. (1963) *J. Med. Chem.*, 6, 85–87): R$_{fD}$ 0.56; RT$_A$ 8.5; AA ratios: Glu 0.93 (1), Gly 0.95 (1), Ala 0.95 (1), Val 1 (Trp and mMel n.d.).

EXAMPLE 8

Boc-mMel-Leu-Gly-Thr-Gln-Trp-Ala-Val-Gly-Leu-Met-NH$_2$ (XIV)

Step 1: Boc-Leu-Gly-OBzl (X)

2.33 ml (20.7 mmol) of NMM and 2.91 ml (20.7 mml) of isobutylchlorocarbonate were successively added to a solution, cooled at −25° C., of 4.8 g (20.7 mml) of Boc-Leu-OH in 70 ml of anhydrous THF. After stirring the reaction mixture for 3 min at ca. −12° C., a cold solution of 6.98 g (20.7 mmol) of H-Gly-OBzl.TsOH and 2.33 ml (20.7 mmol) of NMM in 50 ml of anhydrous DMF was added. The reaction mixture was stirred for 45 min at ca. −12° C. and for 90 min at 0° C., then filtered and evaporated in vacuo. The residue was dissolved in AcOEt and washed several times successively with a 10% aqueous solution of citric acid, brine, a 5% solution of NaHCO$_3$ and brine again. The organic layer was dried over anhydrous Na$_2$SO$_3$ and the solvent removed in vacuo, obtaining 7.8 g (100% yield) of compound X as an oil: R$_{fF}$ 0.83; RT$_A$ 13.6.

Step 2: H-Leu-Gly-OBzl.HCl (XI)

7.4 g (19.6 mmol) of Boc-Leu-Gly-OBzl (X) was deblocked as described in Example 3. The oily residue was ground several times with petroleun ether, obtaining 3.94 g (63.8% yield) of compound XI: R$_{fc}$ 0.59.

Step 3: Boc-mMel-Leu-Gly-OBzl (XII)

5.7 g (12.51 mmol) of Boc-mMel-OH and 3.94 g (12.51 mmol) of H-Leu-Gly-OBzl.HCl (XI) were condensed as described in Example 1-step 2. The residue was dissolved in AcOEt and washed several times successively with a 10% citric acid solution, brine, a 5% NaHCO$_4$ solution and brine again. The organic layer was dried over anhydrous Na$_2$SO$_4$ and the solvent removed in vacuo. The residue was purified by flash chromatography on silica gel, eluting with AcOEt/Et$_2$O=1/7. 6.25 g (75% yield) of product XII were obtained as a foam: R$_{fF}$ 0.80.

Step 4: Boc-mMel-Leu-Gly-OH (XIII)

6.0 g (9.0 mmol) of Boc-mMel-Leu-Gly-OBzl (XII) were treated as described in Example 1-step 3. The residue was ground with AcOEt/Et$_2$O/petroleum ether, giving 4.3 g (83% yield) of compound XIII: R$_{fF}$ 0.43.

Step 5:
Boc-mMel-Leu-Gly-Thr-Gln-Trp-Ala-Val-Gly-Leu-Met -NH$_2$ (XIV)

0.092 g (0.16 mmol) of Boc-mMel-Leu-Gly-OH (XIII) and 0.105 g (0.16 mmol) of H-Thr-Gln-Trp-Ala-Val-Gly-Leu -Met-NH$_2$.HCl (UK Patent Appl. No. 8808768.9, Example 4) were condensed as described in Example 2. After evaporation of the solvent, the residue was dissolved in 10 ml of DMF, poured dropwise in 100 ml of a 10% solution of citric acid, stirred for 15 min, then filtered and washed to neutrality. The crude product was dissolved in 30 ml of DMF and evaporated in vacuo. The residue was ground with DMF/MeOH/AcOEt/Et$_2$O, giving 0.17 g (72.7% yield) of crude compound XIV. A sample was purified by semi-preparative HPLC as described in Example 6: R$_{fC}$ 0.84; RT$_A$ 16.5; AA ratios: Thr 0.94 (1), Glu 1.06 (1), Gly 2.12 (2), Ala 0.94 (1), Val 0.94 (1), Met 1.00 (1), Leu 2, Trp 0.87 (1) (mMel n.d.).

In an analogous manner the following peptides were also synthetized.

(XV): H-pMel-Gln-Trp-Ala-Val-Gly-phe-Leu-Met-NH$_2$.HCl
R$_{fC}$ 0.72; RT$_A$ 9.6.

(XVI): Boc-mMel-Gln-Trp-Ala-Val-Gly-His(Dnp)-Leu-Met-NH$_2$
R$_{fD}$ 0.86; RT$_A$ 21.5; AA ratios: Glu 1, Gly 0.99 (1), Ala 1.03 (1), Val 0.99 (1), Met 1.03 (1), Leu 1.04 (1), Trp 1.05 (1) (mMel and His (Dnp) n.d.)

(XVII): H-mMel-Gln-Trp-Ala-Val-Gly-His-(Dnp)-Leu-Met-NH$_2$.HCl
R$_{fC}$ 0.74; RT$_A$ 9.4; AA ratios: Glu 0.99 (1), Gly 1.04 (1), Ala 1.02 (1), Val 1, Met 0.96 (1), Leu 0.96 (1) (His(Dnp) Trp and mMel n.d.)

(XVIII): Boc-mMel-Gln-Trp-Ala-Val-Gly-His-Leu-Met-NH$_3$.CF$_3$COOH
R$_{fC}$ 0.55; R$_{fD}$ 0.80; RT$_A$ 14.4; AA ratios: Glu 1, Gly 0.99 (1), Ala 0.99 (1), Val 1.06 (1), Met 1.05 (1), Leu 0.97 (1), His 0.90 (1), Trp 1.03 (1) (mMel n.d.)

(XIX): H-mMel-Gln-Trp-Ala-Val-Gly-His-Leu-Met-NH$_2$.2HCl
R$_{fC}$ 0.44; RT$_B$=11.3; AA ratios: Glu 1.00 (1), Gly 1.00 (1), Ala 1.05 (1), Val 1, Met 0.91 (1), Leu 0.89 (1), His 0.99 (1), (mMel and Trp n.d.)

(XX): Boc-mMel-Gln-Trp-Ala-Val-Gly-Leu-Met-NH$_2$
R$_{fC}$ 0.74; RT$_A$ 15.4; AA ratios: Glu 1.03 (1), Gly 1, Ala 1.04 (1), Val 0.96 (1), Met 0.93 (1), Leu 1.02 (1), Trp 0.94 (1) (mMel n.d.)

(XXI): H-mMel-Gln-Trp-Ala-Val-Gly-Leu-Met-NH$_2$.HCl
R$_{fC}$ 0.65; RT$_A$ 5.7

(XXII): H-mMel-Leu-Gly-Thr-Gln-Trp-Ala-Val-Gly-Leu-NH$_2$.HCl
R$_{fC}$ 0.52; RT$_A$ 6.6

(XXIII): H-pMel-Leu-Gly-Thr-Gln-Trp-Ala-Val-Gly-Leu-Met-NH$_2$.HCl (XXIV): H-pMel-Gln-Trp-Ala-Val-ala-His-Leu-Met-NH$_2$.2HCl (XXV): H-pMel-Asn-Gln-Trp-Ala-Val-Gly-Leu-NH$_2$.HCl (XXVI): H-pMel-Asn-Gln-Trp-Ala-Val-Gly-Leu-NH(CH$_2$)$_4$CH$_3$.HCl (XXVII): H-pMel-Arg-Leu-Gly-Asn-Gln-Trp-Ala-Val-Gly-Leu-Met-NH$_2$.HCl (XXVIII): H-pMel-Gln-Arg-Leu-Gly-Asn-Gln-Trp-Ala-Val-Gly-Leu-Met-NH$_2$.2HCl (XXIX): H-pMel-Gln-Arg-Leu-Gly-Asn-Gln-Trp-Ala-Val-ala-Leu-Nle-NH$_2$.HCl (XXX): H-pMel-Gln-Arg-Leu-Gly-Asn-Gln-Trp-Ala-Val-ala-Leu-NH (CH$_2$)$_2$C$_6$H$_5$.HCl (XXXI): H-Glp-Arg-Leu-Gly-pMel-Asn-Gln-Trp-Ala-Val-Gly-Leu-Nle-NH$_2$.HCl (XXXII): H-Leu-Gly-pMel-Gln-Trp-Ala-Val-Gly-phe-Leu-Nle-NH$_2$.HCl (XXXIII): H-Leu-Gly-pMel-Gln-Trp-Ala-Val-Gly-ala-Leu-Nle-NH$_2$.HCl (XXXIV): H-pMel-Asn-Gln-Trp-Ala-Val-Gly-Leu-Leu-NH-NH$_2$.HCl (XXXV): Boc-pMel-Gln-Trp-Ala-Val-Gly-Leu-Met-NH$_2$
Rf$_c$ 0.86; RT$_A$ 15.3; AA ratios: Glu 1.02(1), Gly 1.07(1), Ala 1.10(1), Val 1, Met 0.92(1), Leu 0.98(1) (Trp and pMel n.d.)

(XXXVI): H-pMel-Gln-Trp-Ala-Val-Gly-Leu-Met-NH$_2$.HCl
Rf$_c$ 0.57; RT$_B$ 16.8; AA ratios:Glu 1.08(1), Gly 1.01(1), Ala 0.98(1), Val 1, Met 0.90(1), Leu 0.94(1) (Trp and pMel n.d.)

(XXXVII): Boc-Lys(Boc)-Gly-pMel-Gln-Trp-Ala-Val-Gly-Leu-Met-NH$_2$
Rf$_c$ 0.73; RT$_A$ 18.7; AA ratios: Glu 1.07(1), Gly 2.02(2) Ala 1.18(1), Val 1, Met 0.88(1), Leu 0.95(1), Lys 1.08(1) (Trp and pMel n.d.)

(XXXVIII): H-Lys-Gly-pMel-Gln-Trp-Ala-Val-Gly-Leu-Met-NH$_2$.2CF$_3$COOH
Rf$_E$-0.71; RT$_B$ 15.4; AA ratios: Glu 0.99(1), Gly 2.02(2), Ala 1.00(1), Val 1, Met 0.88(1); Leu 0.91(1), Lys 1.15(1), Trp 0.91(1) (pMel n.d.)

(XXXIX): Ac-Lys(Boc)-Gly-pMel-Gln-Trp-Ala-Val-Gly-Leu-Met-NH$_2$
Rf$_c$ 0.77; RT$_A$ 11.9; AA ratios: Glu 1.05(1), Gly 1.97(2), Ala 0.98(1), Val 1, Met 0.89(1), Leu 0.92(1), Lys 0.92(1), Trp 0.88(1) (pMel n.d.)

(XL): Ac-Lys-Gly-pMel-Gln-Trp-Ala-Val-Gly-Leu-Met-NH$_2$.CF$_3$COOH
Rf$_D$ 0.78; RTB 16.2, AA ratios: Glu 1; Gly 2.11(2); Ala 0.99(1); Val 0.89(1); Met 0.91(1); Leu 0.92(1); Lys 1.10(1) (Trp and pMel n.d.)

(XLI): Boc-pMel-Leu-Gly-Thr-Gln-Trp-Ala-Val-Gly-His(Dnp)-Leu-NH(CH$_2$)$_4$CH$_3$
Rf$_c$ 0.88; RT$_A$ 24.2: AA ratios: Thr 1.04(1), Glu 0.96(1), Gly 2, Ala 1.03(1), Val 0.95(1), Leu 1.92(2) (His(Dnp), Trp and pMel n.d.)

(XLII): H-pMel-Leu-Gly-Thr-Gln-Trp-Ala-Val-Gly-His(Dnp)-Leu NH(CH$_2$)$_4$CH$_3$.HCl
Rf$_c$ 0.50: RT$_A$ 18.7: AA ratios: Thr 0.92(1), Glu 0.97(1), Gly 2.04(2), Ala 1.04(1), Val 1, Leu 1.88(2) (His(Dnp), Trp and pMel n.d.)

(XLIII): Boc-pMel-Gln-Arg-Leu-Gly-Asn-Gln-Trp-Ala-Val-ala-Leu-Nle-NH$_2$.CF$_3$COOH
RT$_A$ 18.4

(XLIV): H-pMel-Gln-Arg-Leu-Gly-Asn-Gln-Trp-Ala-Val-ala-Leu-Nle-NH$_2$.2CF$_3$COOH

TABLE 1

BINDING AFFINITY OF BOMBESIN ALKYLATING ANALOGUES ON MOUSE SWISS 3T3 FIBROBLASTS

| COMPOUND | ID50 (nM) |
|---|---|
| Peptides of the Invention | |
| III | 12,000 ± 400 |
| IX | 8,200 ± 680 |
| VII | 60 ± 20 |
| V | 680 ± 150 |
| XIX | 95 ± 8 |
| XVII | 148 ± 27 |
| VI | 48 ± 2 |
| IV | 1,170 ± 400 |
| XVIII | 40 ± 12 |
| XVI | 390 ± 160 |
| XX | 60.1 ± 3.3 |
| XIV | 445 ± 60 |

TABLE 2

[$H^3$]THYMIDINE INCORPORATION IN MOUSE SWISS 3T3 FIBROBLASTS

| | FOLD INCREASE OVER BASAL VALUE | | | | % INHIBITION IN THE PRESENCE OF 25 nM BBS | | | |
|---|---|---|---|---|---|---|---|---|
| | | | | | A | | B | |
| COMPOUND | 5 nM | 50 nM | 500 nM | 5000 nM | 500 nM | 5000 nM | 500 nM | 5000 nM |
| Peptides of the Invention: | | | | | | | | |
| III | — | — | 1.2 | 1.3 | 0 | 64 ± 10 | 27 ± 14 | 39 ± 7 |
| IX | — | — | 1 | 1 | 0 | 57 ± 13 | 17 ± 4 | 22 ± 3 |
| VII | 2.1 | 4.7 | 4.3 | 4.8 | 6 ± 2 | 17 ± 4 | 57 ± 14 | 61 ± 9 |
| V | 1 | 1 | 1.4 | 1.8 | 26 ± 8 | 44 ± 12 | 87 ± 9 | 83 ± 6 |
| XIX | 1 | 4.1 | 4.3 | 4.4 | 19 ± 7 | 9 ± 5 | 54 ± 1 | 62 ± 6 |
| XVII | 1 | 2.9 | 4.2 | 3.9 | 6 ± 3 | 20 ± 7 | 58 ± 13 | 62 ± 1 |
| VI | 4.1 | 8.0 | 7.0 | 6.6 | 3 ± 2 | 20 ± 3 | 21 ± 3 | 34 ± 5 |
| IV | 1 | 1 | 1.7 | 2.3 | 59 ± 3 | 67 ± 3 | 81 | 73 |
| XVIII | 5.4 | 7.0 | 7.3 | 5.4 | 4 ± 2 | 3 ± 1 | 3 ± 2 | 14 ± 3 |
| XVI | 1.2 | 1.6 | 3.1 | 3.9 | 17 ± 2 | 41 ± 1 | 47 ± 10 | 37 ± 7 |
| VIII | — | 1.1 | 1.2 | 1.2 | 28 ± 6 | 37 ± 4 | 56 ± 3 | 77 ± 11 |
| XX | — | 1.0 | 1.5 | 1.2 | 39 ± 1 | 68 ± 8 | 0 | 35 ± 3 |
| XIV | — | 1.2 | 1.3 | 1.2 | 6 ± 2 | 14 ± 2 | 0 | 32 ± 8 |
| Reference Peptides: | | | | | | | | |
| BBS | 3.0 ± 1 | | | | | | | |
| [Leu$^{13}$ ψ (CH$_2$—NH)Leu$^{14}$]BBS | | | 1.0 | 1.0 | 29 ± 10 | 56 ± 4 | 0 | 0 |

A = analogues are given in combination with BBS
B = cells are pre-treated with analogues, washed, left at 37° C. for 24 h and then challenged with BBS

TABLE 3

PHOSPHORYLATION OF THE p115 PROTEIN ASSOCIATED WITH THE BOMBESIN RECEPTOR

| COMPOUND | MINIMAL ACTIVE DOSE (nM) |
|---|---|
| Peptides of the Invention | |
| III | >10000 |
| VII | 1 |
| V | 100 |
| XIX | 4 |
| XVII | 4 |
| VI | 1 |
| IV | 50 |
| XVIII | 10 |
| XVI | 40 |
| XX | >500 |
| XIV | >1000 |
| Reference peptides: | |
| BBS | 3 |
| Spantide | >10000 |

From the above tables, it is evident that when the alkylating moiety was introduced into an agonist structure (compounds VI, VII, XVIII, XIX) the resulting alkylating analogs increased thymidine incorporation when given alone, and were weak antagonists when given together with BBS but potent antagonists when given 24 hrs before the BBS addition. When the alkylating moiety was introduced into BBS analogues which are "per se" inactive (compounds III and IV) or weak antagonists (compounds IV, V, VIII, XIV, XVI, XVII and XX) the resulting alkylating compounds did not increase incorporation of thymidine and they usually behaved as potent antagonists either when given contemporaneously with BBS or when given 24 hrs after BBS treatment.

What is claimed as new and desired to be secured by Letters Patent of the United States is:

1. A peptide of formula (I):

A-B-C-D-Gln-Trp-Ala-Val-X-Y-T-W   (I)

wherein either:

(i) A represents a hydrogen atom, a Boc group or an acetyl group, one of B and C represents a pMel or mMel residue, and the other of B and C represents a sigma bond or a Gly, Leu-Gly, E-Leu-Gly or Gln-E-Leu-Gly, E, or E-Gly residue with E=Arg(A), arg(A), Lys(A), lys(A), Orn(A) and orn(A); or (ii) A represents a hydrogen atom;
B represents a Glp-Arg-Leu-Gly residue;
C represents a pMel or mMel residue; and
D represents a sigma bond or an Asn or Thr residue;
X represents a Gly or ala residue;
Y represents a sigma bond or a His($R_1$); his($R_1$), Phe, phe, Ser, ser, Ala or ala residue,
T represents a sigma bond or a Leu, leu, Phe or phe residue;
W represents an OH, amino, pentylamino or phenethyl-amino group or a Met-$R_2$, Leu-$R_2$, Ile-$R_2$ or Nle-$R_2$ residue;
$R_1$ represents a hydrogen atom or a Tos, Dnp or Bzl group; and
$R_2$ represents an amino, hydroxy, methoxy or hydrazino group;
or a pharmaceutically acceptable salt of a peptide of formula (I).

2. The peptide of claim 1, said peptide having one of the following formulae:
Boc-pMel-Gln-Trp-Ala-Val-Gly-OH;
Boc-mMel-Gln-Trp-Ala-Val-Gly-OH;

Boc-pMel-Gln-Trp-Ala-Val-Gly-His(Dnp)-Leu-Met-NH₂;
H-pMel-Gln-Trp-Ala-Val-Gly-His(Dnp)-Leu-Met-NH₂;
Boc-pMel-Gln-Trp-Ala-Val-Gly-His-Leu-Met-NH₂;
H-pMel-Gln-Trp-Ala-Val-Gly-His-Leu-Met-NH₂;
Boc-pMel-Gln-Trp-Ala-Val-Gly-phe-Leu-Met-NH₂;
Boc-mMel-Leu-Gly-Thr-Gln-Trp-Ala-Val-Gly-Leu-Met-NH₂;
H-pMel-Gln-Trp-Ala-Val-Gly-phe-Leu-Met-NH₂;
Boc-mMel-Gln-Trp-Ala-Val-Gly-His(Dnp)-Leu-Met-NH₂;
H-mMel-Gln-Trp-Ala-Val-Gly-His(Dnp)-Leu-Met-NH₂;
Boc-mMel-Gln-Trp-Ala-Val-Gly-His-Leu-Met-NH₂;
H-mMel-Gln-Trp-Ala-Val-Gly-His-Leu-Met-NH₂;
Boc-mMel-Gln-Trp-Ala-Val-Gly-Leu-Met-NH₂;
H-mMel-Gln-Trp-Ala-Val-Gly-Leu-Met-NH₂;
H-mMel-Leu-Gly-Thr-Gln-Trp-Ala-Val-Gly-Leu-NH₂;
H-pMel-Leu-Gly-Thr-Gln-Trp-Ala-Val-Gly-Leu-Met-NH₂;
H-pMel-Gln-Trp-Ala-Val-ala-His-Leu-Met-NH₂;
H-pMel-Asn-Gln-Trp-Ala-Val-Gly-Leu-Nle-NH₂;
H-pMel-Asn-Gln-Trp-Ala-Val-Gly-Leu-NH(CH₂)₄CH₃;
H-pMel-Arg-Leu-Gly-Asn-Gln-Trp-Ala-Val-Gly-Leu-Met-NH₂;
H-pMel-Gln-Arg-Leu-Gly-Asn-Gln-Trp-Ala-Val-Gly-Leu-Met-NH₂;
H-pMel-Gln-Arg-Leu-Gly-Asn-Gln-Trp-Ala-Val-ala-Leu-Nle-NH₂;
H-pMel-Gln-Arg-Leu-Gly-Asn-Gln-Trp-Ala-Val-ala-Leu-NH(CH₂)₂C₆H₅;
H-Glp-Arg-Leu-Gly-pMel-Asn-Gln-Trp-Ala-Val-Gly-Leu-Nle-NH₂;
H-Leu-Gly-pMel-Gln-Trp-Ala-Val-Gly-phe-Leu-Nle-NH₂;
H-Leu-Gly-pMel-Gln-Trp-Ala-Val-Gly-ala-Leu-Nle-NH₂;
H-pMel-Asn-Gln-Trp-Ala-Val-Gly-Leu-Leu-NH-NH₂;
Boc-pMel-Gln-Trp-Ala-Val-Gly-Leu-Met-NH₂;
H-pMel-Gln-Trp-Ala-Val-Gly-Leu-Met-NH₂;
Boc-Lys(Boc)-Gly-pMel-Gln-Trp-Ala-Val-Gly-Leu-Met-NH₂;
H-Lys-Gly-pMel-Gln-Trp-Ala-Val-Gly-Leu-Met-NH₂;
Ac-Lys(Boc)-Gly-pMel-Gln-Trp-Ala-Val-Gly-Leu-Met-NH₂;
Ac-Lys-Gly-pMel-Gln-Trp-Ala-Val-Gly-Leu-Met-NH₂;
Boc-pMel-Leu-Gly-Thr-Gln-Trp-Ala-Val-Gly-His(Dnp)-Leu-NH(CH₂)₄CH₃;
H-pMel-Leu-Gly-Thr-Gln-Trp-Ala-Val-Gly-His(Dnp)-Leu-NH(CH₂)₄CH₃;
Boc-pMel-Gln-Arg-Leu-Gly-Asn-Gln-Trp-Ala-Val-ala-Leu-Nle-NH₂; or
H-pMel-Gln-Arg-Leu-Gly-Asn-Glu-Trp-Ala-Val-ala-Leu-Nle-NH₂.

3. A pharmaceutical composition, comprising a peptide of formula (I):

A-B-C-D-Gln-Trp-Ala-Val-X-Y-T-W    (I)

wherein either:
(i) A represents a hydrogen atom, a Boc group or an acetyl group, one of B and C represents a pMel or mMel residue, and the other of B and C represents a sigma bond or a Gly, Leu-Gly, E-Leu-Gly or Gln-E-Leu-Gly, E, or E-Gly residue with E=Arg(A), arg(A), Lys(A), lys(A), Orn(A) and orn(A); or (ii) A represents a hydrogen atom;
B represents a Glp-Arg-Leu-Gly residue;
C represents a pMel or mMel residue;
D represents a sigma bond or an Asn or Thr residue;
X represents a Gly or ala residue;
Y represents a sigma bond or a His(R₁); his(R₁), Phe, phe, Ser, ser, Ala or ala residue,
T represents a sigma bond or a Leu, leu, Phe or phe residue;
W represents an OH, amino, pentylamino or phenethyl-amino group or a Met-R₂, Leu-R₂, Ile-R₂ or Nle-R₂ residue;
R₁ represents a hydrogen atom or a Tos, Dnp or Bzl group; and
R₂ represents an amino, hydroxy, methoxy or hydrazino group;

or a pharmaceutically acceptable salt of said peptide of formula (I), in admixture with a pharmaceutically acceptable diluent or carrier.

4. The pharmaceutical composition of claim 3, comprising as said peptide a peptide having one of the following formulae:
Boc-pMel-Gln-Trp-Ala-Val-Gly-OH;
Boc-mMel-Gln-Trp-Ala-Val-Gly-OH;
Boc-pMel-Gln-Trp-Ala-Val-Gly-His(Dnp)-Leu-Met-NH₂;
H-pMel-Gln-Trp-Ala-Val-Gly-His(Dnp)-Leu-Met-NH₂;
Boc-pMel-Gln-Trp-Ala-Val-Gly-His-Leu-Met-NH₂;
H-pMel-Gln-Trp-Ala-Val-Gly-His-Leu-Met-NH₂;
Boc-pMel-Gln-Trp-Ala-Val-Gly-phe-Leu-Met-NH₂;
Boc-mMel-Leu-Gly-Thr-Gln-Trp-Ala-Val-Gly-Leu-Met-NH₂;
H-pMel-Gln-Trp-Ala-Val-Gly-phe-Leu-Met-NH₂;
Boc-mMel-Gln-Trp-Ala-Val-Gly-His(Dnp)-Leu-Met-NH₂;
H-mMel-Gln-Trp-Ala-Val-Gly-His(Dnp)-Leu-Met-NH₂;
Boc-mMel-Gln-Trp-Ala-Val-Gly-His-Leu-Met-NH₂;
H-mMel-Gln-Trp-Ala-Val-Gly-His-Leu-Met-NH₂;
Boc-mMel-Gln-Trp-Ala-Val-Gly-Leu-Met-NH₂;
H-mMel-Gln-Trp-Ala-Val-Gly-Leu-Met-NH₂;
H-mMel-Leu-Gly-Thr-Gln-Trp-Ala-Val-Gly-Leu-NH₂;
H-pMel-Leu-Gly-Thr-Gln-Trp-Ala-Val-Gly-Leu-Met-NH₂;
H-pMel-Gln-Trp-Ala-Val-ala-His-Leu-Met-NH₂;
H-pMel-Asn-Gln-Trp-Ala-Val-Gly-Leu-Nle-NH₂;
H-pMel-Asn-Gln-Trp-Ala-Val-Gly-Leu-NH(CH₂)₄CH₃;
H-pMel-Arg-Leu-Gly-Asn-Gln-Trp-Ala-Val-Gly-Leu-Met-NH₂;
H-pMel-Gln-Arg-Leu-Gly-Asn-Gln-Trp-Ala-Val-Gly-Leu-Met-NH₂;
H-pMel-Gln-Arg-Leu-Gly-Asn-Gln-Trp-Ala-Val-ala-Leu-Nle-NH₂;
H-pMel-Gln-Arg-Leu-Gly-Asn-Gln-Trp-Ala-Val-ala-Leu-NH(CH₂)₂C₆H₅;
H-Glp-Arg-Leu-Gly-pMel-Asn-Gln-Trp-Ala-Val-Gly-Leu-Nle-NH₂;
H-Leu-Gly-pMel-Gln-Trp-Ala-Val-Gly-phe-Leu-Nle-NH₂;
H-Leu-Gly-pMel-Gln-Trp-Ala-Val-Gly-ala-Leu-Nle-NH₂;
H-pMel-Asn-Gln-Trp-Ala-Val-Gly-Leu-Leu-NH-NH₂;

Boc-pMel-Gln-Trp-Ala-Val-Gly-Leu-Met-NH$_2$;
H-pMel-Gln-Trp-Ala-Val-Gly-Leu-Met-NH$_2$;
Boc-Lys(Boc)-Gly-pMel-Gln-Trp-Ala-Val-Gly-Leu-Met-NH$_2$;
H-Lys-Gly-pMel-Gln-Trp-Ala-Val-Gly-Leu-Met-NH$_2$;
Ac-Lys(Boc)-Gly-pMel-Gln-Trp-Ala-Val-Gly-Leu-Met-NH$_2$;
Ac-Lys-Gly-pMel-Gln-Trp-Ala-Val-Gly-Leu-Met-NH$_2$;
Boc-pMel-Leu-Gly-Thr-Gln-Trp-Ala-Val-His(Dnp)-Leu-NH(CH$_2$)$_4$CH$_3$;
H-pMel-Leu-Gly-Thr-Gln-Trp-Ala-Val-His(Dnp)-Leu-NH(CH$_2$)$_4$CH$_3$;
Boc-pMel-Gln-Arg-Leu-Gly-Asn-Gln-Trp-Ala-Val-ala-Leu-Nle-NH$_2$; or
H-pMel-Gln-Arg-Leu-Gly-Asn-Glu-Trp-Ala-Val-ala-Leu-Nle-NH$_2$.

5. A process for subjecting a patient, in need thereof, to treatment for small cell lung carcinoma, comprising administering to said patient a peptide of formula (I):

$$A\text{-}B\text{-}C\text{-}D\text{-}Gln\text{-}Trp\text{-}Ala\text{-}Val\text{-}X\text{-}Y\text{-}T\text{-}W \quad (I)$$

wherein either:

(i) A represents a hydrogen atom, a Boc group or an acetyl group, one of B and C represents a pMel or mMel residue, and the other of B and C represents a sigma bond or a Gly, Leu-Gly, E-Leu-Gly or Gln-E-Leu-Gly, E, or E-Gly residue with E=Arg(A), arg(A), Lys(A), lys(A), Orn(A) and orn(A); or (ii) A represents a hydrogen atom;
B represents a Glp-Arg-Leu-Gly residue;
C represents a pMel or mMel residue;
D represents a sigma bond or an Asn or Thr residue;
X represents a Gly or ala residue;
Y represents a sigma bond or a His(R$_1$); his(R$_1$), Phe, phe, Ser, ser, Ala or ala residue,
T represents a sigma bond or a Leu, leu, Phe or phe residue;
W represents an OH, amino, pentylamino or phenethyl-amino group or a Met-R$_2$, Leu-R$_2$, Ile-R$_2$ or Nle-R$_2$ residue;
R$_1$ represents a hydrogen atom or a Tos, Dnp or Bzl group; and
R$_2$ represents an amino, hydroxy, methoxy or hydrazino group;
or a pharmaceutically acceptable salt of said peptide of formula (I).

6. The process of claim 5, wherein said peptide is a peptide having one of the following formulae:
Boc-pMel-Gln-Trp-Ala-Val-Gly-OH;
Boc-mMel-Gln-Trp-Ala-Val-Gly-OH;
Boc-pMel-Gln-Trp-Ala-Val-Gly-His(Dnp)-Leu-Met-NH$_2$;
H-pMel-Gln-Trp-Ala-Val-Gly-His(Dnp)-Leu-Met-NH$_2$;
Boc-pMel-Gln-Trp-Ala-Val-Gly-His-Leu-Met-NH$_2$;
H-pMel-Gln-Trp-Ala-Val-Gly-His-Leu-Met-NH$_2$;
Boc-pMel-Gln-Trp-Ala-Val-Gly-phe-Leu-Met-NH$_2$;
Boc-mMel-Leu-Gly-Thr-Gln-Trp-Ala-Val-Gly-Leu-Met-NH$_2$;
H-pMel-Gln-Trp-Ala-Val-Gly-phe-Leu-Met-NH$_2$;
Boc-mMel-Gln-Trp-Ala-Val-Gly-His(Dnp)-Leu-Met-NH$_2$;
H-mMel-Gln-Trp-Ala-Val-Gly-His(Dnp)-Leu-Met-NH$_2$;
Boc-mMel-Gln-Trp-Ala-Val-Gly-His-Leu-Met-NH$_2$;
H-mMel-Gln-Trp-Ala-Val-Gly-His-Leu-Met-NH$_2$;
Boc-mMel-Gln-Trp-Ala-Val-Gly-Leu-Met-NH$_2$;
H-mMel-Gln-Trp-Ala-Val-Gly-Leu-Met-NH$_2$;
H-mMel-Leu-Gly-Thr-Gln-Trp-Ala-Val-Gly-Leu-NH$_2$;
H-pMel-Leu-Gly-Thr-Gln-Trp-Ala-Val-Gly-Leu-Met-NH$_2$;
H-pMel-Gln-Trp-Ala-Val-ala-His-Leu-Met-NH$_2$;
H-pMel-Asn-Gln-Trp-Ala-Val-Gly-Leu-Nle-NH$_2$;
H-pMel-Asn-Gln-Trp-Ala-Val-Gly-Leu-NH(CH$_2$)$_4$CH$_3$;
H-pMel-Arg-Leu-Gly-Asn-Gln-Trp-Ala-Val-Gly-Leu-Met-NH$_2$;
H-pMel-Gln-Arg-Leu-Gly-Asn-Gln-Trp-Ala-Val-Gly-Leu-Met-NH$_2$;
H-pMel-Gln-Arg-Leu-Gly-Asn-Gln-Trp-Ala-Val-ala-Leu-Nle-NH$_2$;
H-pMel-Gln-Arg-Leu-Gly-Asn-Gln-Trp-Ala-Val-ala-Leu-NH(CH$_2$)$_2$C$_6$H$_5$;
H-Glp-Arg-Leu-Gly-pMel-Asn-Gln-Trp-Ala-Val-Gly-Leu-Nle-NH$_2$;
H-Leu-Gly-pMel-Gln-Trp-Ala-Val-Gly-phe-Leu-Nle-NH$_2$;
H-Leu-Gly-pMel-Gln-Trp-Ala-Val-Gly-ala-Leu-Nle-NH$_2$;
H-pMel-Asn-Gln-Trp-Ala-Val-Gly-Leu-Leu-NH-NH$_2$;
Boc-pMel-Gln-Trp-Ala-Val-Gly-Leu-Met-NH$_2$;
H-pMel-Gln-Trp-Ala-Val-Gly-Leu-Met-NH$_2$;
Boc-Lys(Boc)-Gly-pMel-Gln-Trp-Ala-Val-Gly-Leu-Met-NH$_2$;
H-Lys-Gly-pMel-Gln-Trp-Ala-Val-Gly-Leu-Met-NH$_2$;
Ac-Lys(Boc)-Gly-pMel-Gln-Trp-Ala-Val-Gly-Leu-Met-NH$_2$;
Ac-Lys-Gly-pMel-Gln-Trp-Ala-Val-Gly-Leu-Met-NH$_2$;
Boc-pMel-Leu-Gly-Thr-Gln-Trp-Ala-Val-Gly-His(Dnp)-Leu-NH(CH$_2$)$_4$CH$_3$;
H-pMel-Leu-Gly-Thr-Gln-Trp-Ala-Val-Gly-His(Dnp)-Leu-NH(CH$_2$)$_4$CH$_3$;
Boc-pMel-Gln-Arg-Leu-Gly-Asn-Gln-Trp-Ala-Val-ala-Leu-Nle-NH$_2$; or
H-pMel-Gln-Arg-Leu-Gly-Asn-Glu-Trp-Ala-Val-ala-Leu-Nle-NH$_2$.

7. The process of claim 5, comprising administering said peptide in an amount of from about 10 ng kg$^{-1}$ to 10 mg kg$^{-1}$, one to six times daily.

* * * * *